United States Patent [19]
Richards

[11] 4,059,114
[45] Nov. 22, 1977

[54] GARMENT SHIELD

[75] Inventor: Shirley T. Richards, Brooklyn Park, Minn.

[73] Assignee: Minnesota Mining and Manufacturing Company, St. Paul, Minn.

[21] Appl. No.: 734,747

[22] Filed: Oct. 22, 1976

Related U.S. Application Data

[63] Continuation-in-part of Ser. No. 685,769, May 12, 1976, abandoned.

[51] Int. Cl.² ............................................ A61F 13/16
[52] U.S. Cl. .................................. 128/287; 128/290 R
[58] Field of Search ................... 128/284, 287, 290 R, 128/296, 290 P, 290 W, 156

[56] References Cited
U.S. PATENT DOCUMENTS

| | | |
|---|---|---|
| 3,093,546 | 6/1963 | Atkinson ........................... 128/290 R |
| 3,426,754 | 2/1969 | Bierenbaum ......................... 128/156 |
| 3,545,442 | 12/1970 | Wicker ................................. 128/296 |
| 3,732,139 | 5/1973 | Fechillas .............................. 128/296 |
| 3,805,790 | 4/1974 | Kaczmarzk ...................... 128/290 R |
| 3,814,101 | 6/1974 | Kozak ................................... 128/287 |
| 3,881,490 | 5/1975 | Whitehead ...................... 128/290 R |
| 3,888,248 | 6/1975 | Moore .................................. 128/156 |
| 3,903,889 | 9/1975 | Torr ..................................... 128/287 |
| 3,989,867 | 11/1976 | Sisson .................................. 128/296 |

Primary Examiner—Aldrich F. Medbery
Attorney, Agent, or Firm—Cruzan Alexander; Donald M. Sell; Edward T. Okubo

[57] ABSTRACT

A disposable shield for garment protection and everyday feminine hygiene including odor control comprising a very thin, lightweight, highly absorbent structure is disclosed. The shield is soft, rattle-free, supple and easily comformable to the body and the garment and can be securely positioned to the crotch section of a panty or other undergarment.

20 Claims, 5 Drawing Figures

GARMENT SHIELD

BACKGROUND OF THE INVENTION

This application is a continuation-in-part of my copending application Ser. No. 685,769 filed May 12, 1976 and now abandoned.

The present invention relates to the structure and function of a disposable shield particularly suited for everyday feminine hygiene and odor control and for protecting an undergarment against staining from medications and/or daily secretions and discharges which, according to gynecologists may maximally amount to as much as 2 cc. of fluid daily. It comprises a very thin, lightweight, highly absorbent pad which is soft, rattle-free, supple and easily comformable to the body and the garment to which it is adhesively attached. Adhesive attachment of the shield to the crotch section of a panty or other undergarment is easily accomplished by virtue of the adhesive positioning means forming substantially the entire garment facing portion of the shield. Although the holding power of the adhesive structure assures that the shield will not shift and move during wear, removal of the shield leaves no noticeable residue on the undergarment. Disposal of the shield can be accomplished by rolling the body contacting surface to the inside and securing it with the adhesive backing.

The prior art is replete with patents relating to protective pads and shields since the protection of undergarments from staining, especially for the many women who are troubled with frequent and ofttimes daily light bodily discharges has been a long standing problem. These prior patents generally describe layered structures having a porous body contacting layer overlying and confining a layer of absorbent material with an impermeable plastic sheeting as a fluid barrier. To the fluid barrier is attached adhesive strips which after removal of an adhesive protector serve to secure the assembled shield to the crotch portion of an undergarment.

While such prior art devices undoubtedly function to protect the undergarments to which they are applied, they all appear to be deficient in one or more areas of performance.

Generally, the body-contacting layers of the prior art devices are absorbent, porous, dry-laid, nonwoven webs or scrim type materials such as those described by Campau in U.S. Pat. No. 3,044,467, Hendricks in U.S. Pat. No. 3,463,154 and Sneider in U.S. Pat. No. 3,570,491. Such materials are often coarse textured and harsh to the touch and, because of their absorbency, wet from the top surface down during use resulting in a constantly moist surface against the skin.

The unique, soft, comfortable skin-contacting surface of the shield of the present invention which is porous, allows fluid to pass through to the absorbent layer beneath yet will not retain moisture on the surface layer, thus providing greater comfort to the wearer by feeling dry for a longer period of time. The desirability of such a feature has been recognized by Levesque U.S. Pat. No. 3,838,692 who describes a chemical method of providing porosity to hydrophobic materials and by Hoey U.S. Pat. No. 3,887,408 and Meisel U.S. Pat. No. 3,431,911 who suggest the use of chemically treated or crushed foams to achieve the desirable surface properties.

The absorbent layer of prior art examples usually consists of paper fluff as described by Whitehead and Braun in U.S. Pat. No. 3,881,490, some of high absorbency fiber wadding referred to by Sneider in U.S. Pat. No. 3,570,491, or plies of tissue as used by Campau and described in U.S. Pat. No. 3,044,467. In these examples the composite structure is adhesively unified.

In contrast, in the embodiments of the present invention where a blend of absorbent fibers or fluff with thermoplastic fibers is utilized, it is possible to unify the composite structure by heat bonding or sonic welding while still maintaining the loft and fluid holding capacity of the structure.

The present invention also provides a vapor permeable liquid barrier to prevent staining of the undergarment while allowing for the evaporation of moisture vapor thus ameliorating the hazards of heat and moisture buildup which are known to encourage the group of bacteria.

Tyrell U.S. Pat. No. 3,315,677 describes a waterproof ply of polyethylene and Hendricks U.S. Pat. No. 3,463,154 advocates the use of a liquid-repellent layer of tissue paper with a thin outer layer of vinyl or polyethylene. Whitehead and Braun U.S. Pat. No. 3,881,490 suggests the use of a plastic film backing and Sneider U.S. Pat. No. 3,570,491 uses a 5-mil polyethylene plastic film backing to prevent fluid penetration to the garment. None of these patents even suggests the desirability of permitting passage of moisture vapor through the shield and the added protection and comfort to the wearer that can be thereby obtained.

The existing patent art for daily feminine protection appears to be devoid of any recognition of the health hazards resulting from excessive microbial growth or the disruption of the normal microbial balance in the vaginal area by the use of certain deodorant soaps and sprays sometimes used to eliminate odors and provide an aura of freshness to the wearer. The shield of the present invention addresses these very basic concerns by the incorporation of antimicrobial and odor control agents therein. It is to be understood that as used herein, antimicrobial agent refers to any material which is inhibitory to the growth and/or reproduction of microorganisms, the latter being understood to include bacteria, fungi and yeasts.

Secure positioning, with complete removal of the attaching adhesive, has long been desired and the prior art has many statements of the fact being accomplished; yet it is well known, by the users of the shields and pads designed to prevent staining of garments, that the pads and shields shift and move during wear and that the adhesives do leave adhesive residue on the undergarment.

Sneider U.S. Pat. No. 3,570,491 is directed to a pad having a contact adhesive over "substantially" the full surface thereof. Significantly, the patentee requires an adhesive-free periphery and nonchalantly considers that any adhesive residue remaining on the garment upon removal of the pad is unimportant since the adhesive is nontoxic. Campau U.S. Pat. No. 3,044,467 advocates the use of strips of adhesive located at the ends of the pad for secure positioning. Hendricks U.S. Pat. No. 3,463,154 describes the use of strips of adhesive on the peripheral end portions of the shield. Sargent U.S. Pat. No. 3,595,237 describes a pad held in position by a strip of patterned high-tack adhesive extending from one end of the pad to the other.

The shield of the present invention provides for greater placement security and comfort through the use of a pressure-sensitive adhesive coating over the entire garment attaching surface which assures against movement of the shield or the folding of edges during the use of the pad thus adding to the comfort and secure feeling of the wearer.

One of the important considerations in a disposable product which will likely be used daily is price which bears a direct relationship to the cost of manufacture. Pads such as those described by Sneider and Hendricks, which utilize layers of different sizes to prevent fluid from seeping through the pad edges onto the underlying garment, require assembly of the pads in a manner requiring much greater manufacturing precision than the shields of the present invention wherein fluid flow is controlled by utilizing the wicking characteristics of the fibers by compressing them in line-embossed patterns at the same time the shield edges are bonded.

SUMMARY OF THE INVENTION

The disposable shield of the present invention comprises a small, thin, comfortably shaped, highly absorbent pad having a body-contacting surface, an absorptive portion, a liquid barrier and positioning means for securely yet removably attaching the shield to an undergarment.

The body-contacting surface is a porous, substantially planar flexible polymeric coating on the surface of a bonded staple hydrophobic fiber web or the outermost surface of a lofty web of blended fibers in an integral pad construction. Such a surface, due to the flatness of the polymeric coating, has an unusually soft, smooth feeling and is pleasing to the touch.

The absorptive portion of the shield of one embodiment of the present invention comprises a spatially controlled blend of (1) absorbent cellulose paper fluff and (2) a hydrophobic textile fiber distributed in a web weighing 60 to 160 pounds per 320 square yards. The web is formed with a greater proportion of nonabsorbent textile fibers on the surface which will be in contact with the top web for the purpose of controlling the area of greatest absorption to thus optimize the comfort to the wearer by keeping the upper surface dry longer. It will, of course, be appreciated that the absorptive portion of the shield may be the central portion of an integrally formed pad member having a porous, planar, flexible polymeric coating as its top surface. In other embodiments of the present invention, the absorptive portion of the shield can utilize a variety of water immobilizing materials to increase fluid capacity or minimize pad bulk.

While it is important to eliminate the unchecked microbial growth which can proliferate under warm, moist conditions, it is equally important to insure that normal microbial balance of the vaginal area is maintained for optimum feminine hygiene. In order to achieve this balance, the shield is treated with an antimicrobial agent whose purpose it is to retard the growth and/or reproduction of microorganisms which may otherwise occur when any discharge is retained within the absorbing layer. Not only does the incorporation of an antimicrobial agent aid in maintaining proper microbial balance, but the elimination of excessive microbial growth minimizes any odor resulting from the metabolic by-products of such growth. Additionally, to assure the wearer that any residual odor will not be perceived, a malodor counteractant can be added to the interior portion of the shield.

The moisture barrier comprises a soft, pliable, rattle-free, moisture vapor-permeable but body fluid-impermeable web formed of blown microfibers such as polypropylene. The moisture barrier could also be a fiber reinforced layer of a rubbery film-forming polymer such as butadiene-styrene.

The positioner means preferably comprises a moisture vapor permeable adhesively coated dry-laid web which can be securely attached to fabrics normally made into undergarments and is capable of being easily removed therefrom without fabric damage or leaving noticeable adhesive residue thereon.

The shield of the present invention is produced by assembling the component parts thereof, unifying the composite by bonding with heat and pressure and then cutting to a shape offering the greatest absorptive area while minimizing excessive material which can cause bunching and discomfort to the wearer.

BRIEF DESCRIPTION OF THE DRAWINGS

In the accompanying diagrammatic drawings which illustrate the invention.

DETAILED DESCRIPTION OF THE INVENTION

Figure 1:
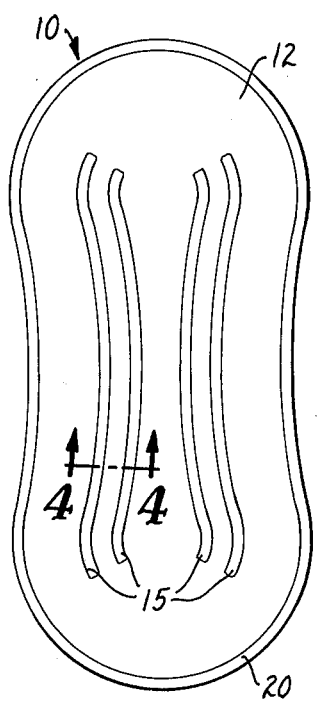
FIG. 1 is a plan view of one embodiment of a shield of the present invention.

Referring now more particularly to the drawings, FIG. 1 shows a shield of the present invention in plan view. The shield there shown has a generally panduriform shape. Other shapes are shown in FIGS. 2 and 3 and many others will suggest themselves.

Figure 2:
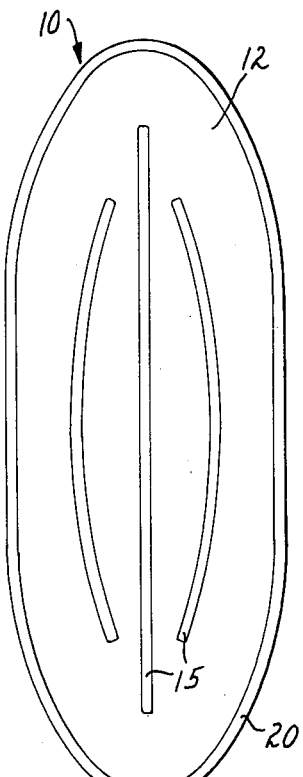
FIGS. 2 and 3 are plan views of two modified shield shapes.
Figure 3:
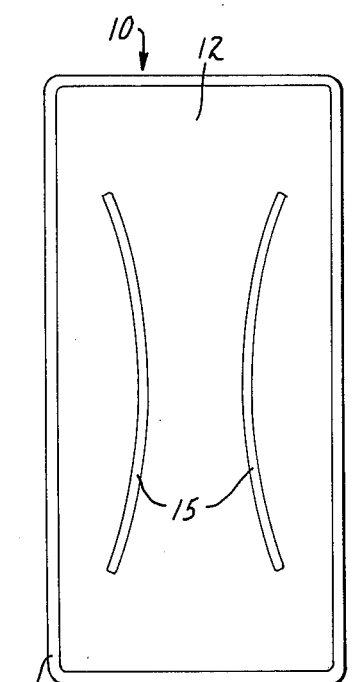

In the plan view of FIGS. 1 to 3, there is shown an elongate shield 10 having a body-contacting surface 12 with a pattern of spaced longitudinally extending line embossments 15 impressed therein.

Figure 4:
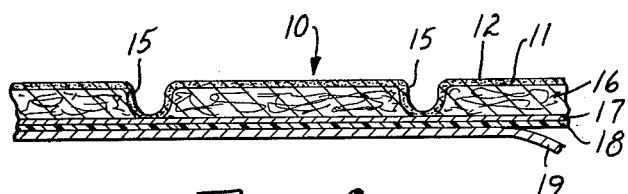
FIG. 4 is an enlarged section taken along line 4—4 of FIG. 1.
Figure 5:
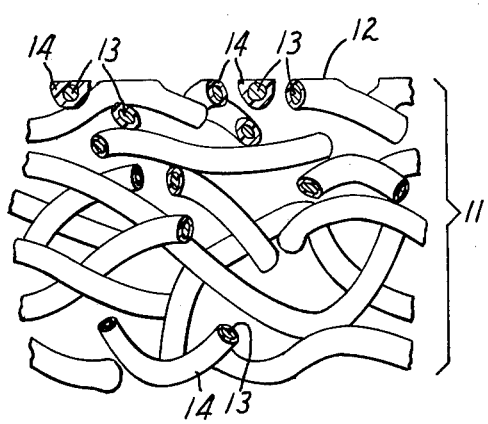
FIG. 5 is a greatly enlarged section of the top web of the shield of FIG. 4.

The upper layer 11 with its body-contacting surface 12, in the embodiment shown in FIGS. 4 and 5, comprises a nonwoven fibrous web formed of staple hydrophobic textile fibers unified by being coated with a water-insoluble rubbery fiber-binding resin so that all of the individual fibers 13 are substantially covered with a resin coat 14, thus bonding them together at their crossing points while leaving the interstices of the web unfilled.

The resulting web is a thin, pliable, relatively inextensible, resilient, hydrophobic, porous, clothlike fabric whose top surface has an unusually soft, smooth, pleasing, doe skin-like tactile quality. It is believed that the pleasing qualities of the body-contacting surface result from the flatness of the surface caused by having been supported by the smooth surfaced release paper during the drying cycle of the coated web since the surface exposed to the heat has the more traditional hand of a typical bonded nonwoven fabric.

The internal structure of one embodiment of a shield 10 according to the present invention is shown in FIG. 4. Immediately below and in heat-bonded relationship with body-contacting layer 11 is a web 16 formed of a spatially controlled blend of hydrophilic absorbent cellulose paper fluff and hydrophobic nonabsorbent textile fibers, so that a greater proportion of nonabsorbent fibers is present in the web 16 at the surface which is in contact with layer 11. In this manner, the upper or body-contacting surface of shield 10 will be kept dry for a longer period.

The difference in wettability of the two surfaces of the fibrous batt can be shown by placing a drop of water onto each surface and observing the time to lose specular reflection, but most importantly, by noting the wetted area on both the drop side and the opposite side, the diffusion of the drop within the batt and its passage towards an absorbent towel placed beneath the batt.

The differential wetting characteristics of the two surfaces of this unstabilized and unbonded structure thus provide for controlled movement of fluid away from the hydrophobic face of the shield with minimal wetting of the upper surface. The nonabsorbent fibers adjacent to layer 11 further assist in carrying moisture away from the body thus optimizing the comfort to the wearer by keeping the upper surface drier to the touch.

Surprisingly, even though the structure contains a substantial proportion of hydrophobic fibers, it will retain a greater quantity of fluid than an equivalent weight structure formed entirely of hydrophilic paper fluff. Thus, in comparative tests, an absorptive layer of 115 pound per 320 square yards basis weight (0.1158 gram per square inch), was found to retain 9.36 times its weight of fluid. In contrast, the absorptive layer of a commercially available product used for garment protection during light flow of the menses, weighing 0.1106 gram per square inch (calculated) retained 6.39 times its weight of fluid. Both tests were conducted following the general procedure outlined in the Absorbency and Pressure Tests Methods developed by Grain Processing Corp. (published in *Nonwovens & Disposable Soft Goods*, August 1973, page 8), in which retained fluid is measured after saturation, and following compression at 1 psi (approximately body pressure in use).

In other embodiments of the present invention the absorptive portion of the shield may advantageously utilize a blend of cotton/polyester or paper fluff/polyester constructions with highly absorbent cross-linked carboxymethyl cellulose fibers such as CLD 40 from Buckeye Cellulose Corp. or Aqualon Fibers from Hercules, Inc. It is also contemplated that water immobilizing polyacrylate materials such as Dow Chemical Company's Polymer XD 8587 could be sprayed in liquid form onto the barrier contacting web surface to increase the fluid holding capacity of the pad or to allow for adequate absorption with a lighter weight fiber batt. Since the polyacrylate materials are film-formers, a water-swellable film with a suitable moisture wicking carrier such as a creped tissue could provide adequate fluid containment between the adhesive/barrier layer and a thin, porous, hydrophobic surface layer. Such a material is available as XD 30106 from Dow Chemical Co. In still another embodiment of the present invention, the absorptive portion of the shield could be a sheet of absorbent tissue, to which is affixed a pattern of a hydrolyzed starch-polyacrylonitrile graft copolymer. In this configuration, the tissue serves to wick the fluid to areas of absorption by the starch polymer. A commercially available product of this type is identified as 35-A-100 from Grain Processing Corp. Additionally, printing of the absorbent onto the pad barrier layer has been found to be a feasible method of increasing fluid capacity or minimizing pad bulk.

As earlier noted, an antimicrobial agent is preferably incorporated into the absorbing layer of the web. It has been found that by applying a 2% solution in acetone of a propyl ester of parahydroxybenzoic acid (available as Tri-Kem Propyl Paraben from Tri-Kem, Inc. of Westwood, N.J.), to the absorbing portion of the shield at a level of about 20 grams per square foot, the resulting shield effectively prevents the growth of *Candida albicans*, a typical organism found in the vagina, using AATCC Test Method 100-1970.

As an odor controller, either for use in conjunction with the antimicrobial agent or alone, we have found that a 1,25% isopropyl alcohol solution of "Ozone Bouquet" 96025 (Monsanto Co.) applied at a level of about 20 grams per square foot to the inner surface of the absorptive layer effectively prevented the sensing of malodorous agents such as n-valeric acid, urea and 1,4-butanedithiol.

The antimicrobial agent and odor controller hereinabove described can be easily added to the hydrolyzed starch-polyacrylonitrile graft copolymer or the other chemical absorbents thus insuring intimate contact with any fluids absorbed and held in the shield.

As clearly seen in the drawings, line embossments 15 do not exceed to the edges of the shield 10. In this manner absorbed fluid is prevented from wicking onto the undergarment to which the shield is adhesively attached.

In immediate juxtaposition to and coterminous with web 16 is a fluid barrier 17 in the form of a soft, pliable, rattle-free, moisture vapor permeable but body fluid impermeable layer of a blown microfiber web. Shields having such a barrier layer will allow moisture vapor to pass through the pad at a rate of 7850–8500 grams/meter$^2$ per 24 hours period as tested under conditions of 100° F. and 95% R.H., using the ASTM E-96-53 testing procedure. The same barrier material prevents the passage of fluid to an absorptive undersurface as can be illustrated by placing 2 milliliters of a fluid (viscosity: 2 centipoises; surface tension: 48.7 dynes per centimeter; solid content: 0.6 percent) slowly, in a dropwise manner, upon the upper surface of the shield, which has been placed upon an absorptive white towel, allowing the fluid to penetrate and be retained by the shield, placing a flat metal pressure plate upon the 2 × 4 inch shield surface and then loading the pressure plate with 3632 grams of weight (1.0 psi). Continuous pressure is maintained for 60 minutes. Following removal of the weights, plate and pad, the lack of penetration of the fluid to the towel can be easily observed.

The barrier layer 17 could also be a fiber reinforced layer of a rubbery film-forming polymer such as butadiene-styrene copolymer. A shield with such a material incorporated therein has a moisture vapor transmission value of about 240 grams/m$^2$/24 hours. This barrier layer was also found to prevent the passage of fluid when tested as above described.

Both examples effectively prevent the passage of fluid through the shield when in actual use.

Positioner means 18, in the form of a dry-laid nonwoven web saturated with a pressure-sensitive adhesive composition on a protective liner 19, is attached to fluid barrier 17. In order for the adhesive of positioner means 18 to function effectively under the conditions to which it is subjected and on the fabrics it will be contacting, not only is the selection of the adhesive itself important but also the intricate adhesive system must be balanced as to surface adhesion, compliancy, coating weight, backing adhesion and backing strength. To remove cleanly from the garment to which it is attached, the adhesive bond to the garment surface must be weaker than the cohesive strength of the adhesive per se, the bond strength of the adhesive to its backing material, and the intrinsic strength of the composite structure.

In general, we have found that for a shield not to dislodge, shift or move during wear, it usually requires a minimum 180° peel force of 1.5 ounces per inch width when peeled from 40 denier nylon tricot at 12 inches per minute and a minimum shear force of 20 ounces per square inch of contact when sheared from 40 denier nylon tricot at 2 inches per minute. The greater the area of the shield covered with the adhesive, the lower the values can be per inch width. An overall adhesive coating as the garment attaching surface enhances the security and comfort of the shield by attaching most of the surface to the garment thus preventing bunching, folding, slipping and unintentional detachment.

The component parts of the shield 10 are assembled in the order illustrated in FIG. 4 and unified by heat-sealing with a metal die platen configured with the desired shape of the shield and line embossments 15 thereon. Shields 10 are then trimmed to shape and size along heat seal line 20, each shield typically being about 8 square inches in area.

The following Examples will serve to further illustrate the present invention:

EXAMPLE 1

A. Surface and Absorptive Layer

A blend of 1.75 dpf, 1½ inch length polyester staple fiber made by the Celanese Corporation and a scoured and bleached 4.9 micronaire cotton (grade 52-staple 32) fiber, each comprising about 50 percent of the total weight, is formed into a continuous fluffy web on airlaying web equipment such as a "Rando-Webber" machine, sold by the Curlator Corp., to a uniform web whose weight is about 125 pounds per 320 square yards. A garnett machine or carding machine may also be used for web formation.

A dispersion of web bonding resin is prepared by blending the following materials in a mixing vessel at room temperature:

| | |
|---|---|
| Polyethyl acrylate ("Rhoplex" HA-8, Rohm & Haas) | 540 ml |
| Ethylene-vinyl acetate copolymer ("Elvace" 1875, dupont) | 60 ml |
| Octylphenoxy polyethoxy ethanol ("Triton" X-100, Rohm & Haas) | 5 gm |
| Sodium salt of condensed arylsulphonic acid ("Tamol" 731 - 25%, Rohm & Haas) | 10 gm |
| Ethyl acrylate-acrylic acid copolymer ("Acrysol" - ASE-60, Rohm & Haas) | 60 gm |
| Ammonium hydroxide - 28% | 25 gm |
| Water | 2400 ml |

The solids content of the resulting solution is about 10% with a viscosity of about 46–47 centipoises. The fibrous batt is passed through a solution-applying set of nip rolls at a speed of about 5 feet per minute to unify the surfaces of the fluffy web. The top solution-applying roll is a 50-line grooved roll of 90° included angle and a b 0.0065 inch depth, excess solution being removed from the roll surface by a doctor blade. A release backing, such as a Weyerhaeuser Company's semi-bleached 43-pound "S/N 61" C1S silicone coated release paper, passes through the solution, around the bottom roll, through the nip, then through the drying oven. A small quantity of solution, ranging from about 0.05 to 0.10 pound per square yard, is carried from the solution bath up to the nip of the rolls by the release backing. A flexible 1½ mil polyester wiping film extends across the width of the lower nip roll to level and to unify the liquid layer carried by the release backing. The fluffy batt of fibers from the Rando-Webber machine is fed into the nip and its bottom surface is pressed onto the fluid layer. Simultaneously, the upper surface of the fibrous batt is wetted with solution by the top roll. The nip roll pressure exerted on the fibrous batt is about 35 pounds per lineal inch width of roll.

The composite structure (coated fibrous batt plus release backing) is then dried in an air circulating oven at a temperature of 250° F. for a period of about 5 minutes. The hot air is directed downwards onto the exposed fiber surface with little or no air directed toward the bottom surface of the release paper. The dried batt is removed from the release paper as it passes out of the oven. The surface of the web adjacent to the release backing is found to be porous, substantially flat or planar in nature and exhibits an unusually soft, smooth, pleasing doe skin-like tactile quality. The opposite exposed surface of the web is resin-unified but has a fibrous, more characteristic nonwoven fabric texture. The web has a finished weight of about 118 pounds per 320 square yards, a thickness of about 0.5 inch to 0.6 inch, and a resistance to the passage of air of about 0.16 inch of water at 100 feet per minute air face velocity.

B. Fluid Barrier and Positioning Means

The fluid barrier and positioning means are prepared by coating a release liner such as Weyerhaeuser Co.'s semi-bleached 45-pound "S/N 61" C1S silicone-coated paper with a solution of a pressure-sensitive adhesive such as that described by Ulrich in U.S. Pat. No. 2,844,126 to a dry weight of about 3 grains per 4 × 6 inch. A reinforcing paper, known in the trade as 8 "Crystex" Tissue and supplied by Crystal Tissue Co., is applied to the dry adhesive and the exposed tissue is coated with a film-forming polymer such as Polyco 556w butadiene-styrene latex by standard coating techniques such as knife coating, wire bar coating, rotogravure, squeeze roll, etc., to a dry weight of about 5 grains per 4 × 6 inch. The structure is then oven dried at 160° F. for about 10 minutes.

A heated sealing metal die platen is used to unify the pad which is formed by superposing the fibrous web on the barrier/positioner/liner structure with the soft, body contacting surface of the composite against the die. On a Wabash Hydraulic Press — Model 75 — 152TM, adequate sealing is obtained using 500 psi per 6-inch diameter ram at 350° F. for 3 to 5 seconds. Shields were thus produced having the shapes shown in FIGS. 1 to 3.

EXAMPLE 2

A. Surface Layer

A dry-laid nonwoven web is prepared on a RandoWebber from 1.75 dpf, 1½ inch length polyester staple fibers to give a fabric weight of from 10 to 15 pounds per 320 square yards. This web is treated by the means previously described and with the same resin solution to about 3.5 to 4 times the fiber weight. The composite is ovendried at 250° F. for 5 minutes. The heated air is directed downward onto the exposed fiber. The unified web is removed from the release liner and the web surface contacting the release liner is found to have the doe skin character of Example 1.

B. Absorptive Layer

A mixture of about 20% of 3 dpf polyester staple fibers of 1½ inch length and 80% bleached sulfite kraft paper fluff by weight is deposited (in a manner similar to that described by Mesek and Repke in U.S. Pat. No. 3,768,480) to give a web whose weight is about 120 pounds per 320 square yards. The air flow velocity is adjusted so that some separation of the two types of fibers takes place. As the batt is formed, the polyester fiber dominates the character of the bottom surface of the web and the paper fluff the top surface.

C. Fluid Barrier

A thin layer of melt-blown polypropylene fibers is prepared as described in the Naval Research Lab Report 4364 — May 25, 1964 so that it has a weight of from about 0.04 to 0.06 pound per square yard and a flow resistance of about 0.4 inch of water at an air face velocity of 100 feet per minute.

D. Positioner Layer

A dry-laid web is prepared from a blend of about 20% 1.75 dpf, 1½ inch polyester staple fiber and about 80% 1.5 dpf, 1½ inch length rayon staple fiber at a total weight of about 15 lbs. per 320 square yards. This web is saturated in the manner previously described for the surface layer in this Example but with an adhesive solution of the following composition:

| | |
|---|---|
| Vinyl acetate/2-ethylhexyl acrylate-methyl acrylate ("Film Grip" 68-13-D, Stein Hall Co.) | 1000 ml |
| "Acrysol" ASE-60 | 40 gm |
| Ammonium hydroxide - 28% | 25 gm |
| Water | 2000 ml |

The solids content of the solution is about 19% and the viscosity is 31 centipoises. The solution add-on is about four times the fiber weight and the finished weight is about 21 pounds per 320 square yards. The liner is not removed to expose the pressure-sensitive adhesive until the shield is ready for placement on the undergarment.

The four-layer composite, namely, the surface layer, absorptive layer, fluid barrier and positioner/liner layer, is unified by heat sealing as in Example 1. The shield is then trimmed to size.

EXAMPLE 3

The resin-unified web and absorptive layer of Example 2 are combined with the composite fluid barrier/positioner/liner layer of Example 1, heat sealed in the manner hereinbefore described, and trimmed to size to form a shield according to the present invention.

EXAMPLE 4

The resin-unified composite body-contacting and absorptive web of Example 1 is layered with the fluid barrier web and positioner means of Example 2 and heat sealed and trimmed to produce a shield of the present invention.

EXAMPLE 5

A. Surface Layer

A dry-laid nonwoven web is prepared from 3 dpf polyester fiber of 1½ inch length on a Rando-Webber to give a finished weight of about 45 pounds per 320 square yards after saturation and drying.

The fibrous web is treated in the manner described in Example 1 but with the following solution:

| | |
|---|---|
| "Rhoplex" HA-8 | 540 ml |
| "Elvace" 1875 | 60 ml |
| Water | 2400 ml |
| "Acrysol" ASE-60 | 65 gm |
| "Tamol" 731-25% | 20 gm |
| "Triton" X-100 | 5 gm |
| Ammonium Hydroxide - 28% | 25 gm |

The solids content was 10.7% and the viscosity about 57 to 62 centipoises. The wet solution pickup was about 2.9 times the fiber weight. The fluid penetration time of the finished web was 1 to 2 seconds and the resistance to air flow was about 0.05 inch of water. The unified web had the desirable surface characteristics of Example 1.

B. Absorptive Layer

A mixture of 3 dpf 1½ inch polyester staple fiber (20%) and bleached sulfite paper pulp (80%) was formed as in Example 2 at a weight of about 60 pounds per 320 square yards.

C. Fluid Barrier and Positioning Means

The structure described in Example 1 was used.

D. Assembly

The three-layer composite, namely the surface layer, absorptive layer, and fluid barrier/positioning layer, are unified by heat sealing as in Example 1.

EXAMPLE 6

The surface layer and absorptive layer of Example 5 are layered with the fluid barrier and positioning means of Example 2, heat sealed and trimmed to form a shield of the present invention.

EXAMPLE 7

The resin-unified composite body contacting and absorptive web of Example 1 is combined with a fluid barrier/positioner/liner layer comprised of a flexible 1/32 inch thick Type E polyethylene closed cell foam of 4 pounds per cubic foot density (purchased from Voltek Corp.), coated with about 3 grains per 4 × 6 of the adhesive of Example 1, heat sealed and trimmed to size as previously described.

Although the fluid barrier of the shields of this Example are air impervious, they were found to function well as a garment protector.

EXAMPLE 8

The resin-unified web of Example 2 is combined with a 1.5 mils polyacrylate film available from Dow Chemical Co. as XD 30106 overlying a creped tissue moisture-wicking carrier (the tissue being in contact with the lower surface of the web), and heat sealed to the composite fluid barrier/positioner/liner structure of Example 1 and trimmed to form a shield according to the present invention.

EXAMPLE 9

The resin-unified web of Example 2 or 5 is combined with a sheet of absorbent tissue having thereon a pattern of a hydrolyzed starch-polyacrylonitrile graft copolymer (35-A-100 available from Grain Processing Corp.) and heat sealed to the composite fluid barrier/positioner/liner layer of Example 1 and trimmed to form a shield according to the present invention. The shield performed satisfactorily and the absorbent tissue served to wick the moisture to the starch polymer pattern.

EXAMPLE 10

The barrier contacting surface of a resin-unified web of Example 1, in about an 80 pound per 320 square yards weight, is sprayed with about 8.0 – 8.5 grams per square yard (dry basis) of a water immobilizing polyacrylate material, available from Dow Chemical Co. as Polymer XD 8587. The web is then combined with the composite fluid barrier/positioner/liner layer of Example 1 and the assembled laminate is sonically welded and then trimmed to form a shield according to the present invention. The shield thus formed is extremely thin and lightweight yet easily absorbs and retains the "required" 2 ml. of fluid.

While most of the discussion herein has been directed to heat sealing of the composite structures to form shields according to the present invention, it is to be understood that sonic welding techniques have also been utilized to form shields and is contemplated as being fully equivalent to heat sealing.

What is claimed is:

1. A disposable shield for everyday feminine hygiene and garment protection comprising a thin, elongate, highly absorbent pad having (a) a porous, substantially planar hydrophobic polymeric body-contacting surface having a soft, doe-skin like hand, (b) an absorptive portion having differential wetting characteristics from one surface to the other to thus provide for controlled movement of fluid away from the bodycontacting surface, (c) a soft, pliable, rattle-free, body fluid-impermeable barrier and (d) an adhesive positioner means comprising substantially the entire garment-contacting surface, said shield being adapted for attachment to a garment such that the shield will not dislodge, shift or move during wear but is removable from the garment without fabric damage or adhesive residue.

2. A disposable shield according to claim 1 wherein said body-contacting surface is the uppermost surface of a lightweight nonwoven web of hydrophobic, thermoplastic fibers unified with a resinous fiber-binding resin.

3. A disposable shield according to claim 1 wherein the absorptive portion comprises a web of 1:1 blend of polyester staple fibers and cotton staple fibers.

4. A disposable shield according to claim 1 wherein the absorptive portion comprises a web of a 1:1 blend of polyester staple fiber and cotton staple fibers, to which is added a small amount to highly absorbent fluid immobilizing fibers.

5. A disposable shield according to claim 2 wherein the absorptive portion comprises a web of a 20:80 spatially controlled blend of polyester staple fibers and bleached sulfite kraft paper fluff, the uppermost surface of said web being predominantly hydrophobic polyester fibers.

6. A disposable shield according to claim 2 wherein the absorptive portion comprises a web of 20:80 spatially controlled blend of polyester staple fibers and bleached sulfite kraft paper fluff, to which is added a small amount of highly absorbent fluid immobilizing fibers, the uppermost surface of said web being predominantly hydrophobic polyester fibers.

7. A disposable shield according to claim 2 wherein the absorptive portion comprises a sheet of absorbent tissue having laminated thereto a water-swellable film of a water-immobilizing polyacrylate polymer.

8. A disposable shield according to claim 1 wherein the absorptive portion comprises a sheet fo absorbent tissue to which is affixed a pattern of a highly moisture-absorbent hydrolyzed starch-polyacrylonitrile graft copolymer.

9. A disposable shield according to claim 1 wherein the absorptive portion comprises a patterned layer of a hydrolyzed starch-polyacrylontrile graft copolymer applied onto the body fluid impermeable barrier.

10. A disposable shield according to claim 1 wherein the body fluid-impermeable barrier is moisture vapor-permeable.

11. A disposable shield according to claim 6 wherein the body fluid-impermeable barrier is a web of entangled melt-blown organic polymeric microfibers.

12. A disposable shield according to claim 6 wherein the body fluid-impermeable barrier is a thin layer of a film-forming polymer.

13. A disposable shield according to claim 1 wherein the body fluid-impermeable barrier is a thin foam.

14. A disposable shield according to claim 1 wherein the positioner means comprises a fiber reinforced pressure-sensitive adhesive layer overlying substantially the entire surface of said body fluid-impermeable layer.

15. A disposable shield according to claim 1 wherein the positioner means comprises a nonwoven web unified with a pressure-sensitive adhesive composition.

16. A disposable shield according to claim 1 having a pattern of longitudinally extending line embossments terminating within the periphery of the shield impressed in said body-contacting surface and said absorptive portion to channel fluid toward the ends of the shield.

17. A disposable shield according to claim 1 having an antimicrobial agent incorporated into the absorptive thereof.

18. A disposable shield according to claim 1 having a malodor counteractant incorporated into the absorptive layer thereof.

19. A disposable shield for everyday feminine hygiene and garment protection comprising a thin, elongate, highly absorbent pad having:
a. a porous, substantially planar bodycontacting surface having a soft doe-skin like hand,
said surface being the uppermost surface of said pad unified with a hydrophobic resinous fiber binding resin;
b. an absorptive portion comprising a lofty web of a 1:1 blend of polyester staple fibers and cotton staple fibers having differential wetting characteristics from one surface to the other to thus provide for controlled movement of fluid away from the body-contacting surface.
said absorptive portion having an antimicrobial agent and a malodor counteractant incorporated therein;
c. a thin, soft, pliable, rattle-free, moisture vapor-permeable but body fluid-impermeable barrier,
said barrier being a thin layer of a film-forming polymer,
d. an adhesive positioner means overlying said barrier and comprising substantially the entire garment contacting surface,
said positioner means being a fiber-reinforced pressure-sensitive adhesive layer;
e. a pattern of longitudinally extending line embossments terminating within the periphery of the shield impressed in said body-contacting surface and said absorptive portion to channel fluid toward the ends of the shield, said shield being adapted for attachment to a garment such that the shield will not dislodge, shift or move during wear but is removable from the garment without fabric damage or adhesive residue.

20. A disposable shield for everyday feminine hygiene and garment protection comprising a thin, elongate, highly absorbent pad having:
 a. a porous, substantially planar body-contacting surface having a soft doe-skin like hand,
   said surface being the uppermost surface of a lightweight nonwoven web of hydrophobic, thermoplastic fibers unified with a hydrophobic resinous fiber binding resin;
 b. an absorptive portion comprising a lofty web of a 20:80 spatially controlled blend of polyester staple fibers and bleached sulfite kraft paper fluff, the top surface of said web being predominantly hydrophobic polyester fibers, said web having differential wetting characteristics from one surface to other to thus provide for controlled movement of fluid away from the body contacting surface, said absorptive portion having an antimicrobial agent and a malodor counteractant incorporated therein;
 c. a thin, soft, pliable, rattle-free, moisture vapor-permeable but body fluid-impermeable barrier,
   said barrier being a thin web of entangled melt-blown organic polymeric microfibers;
 d. an adhesive positioner means overlying said barrier and comprising substantially the entire garment contacting surface,
   said positioner means being a nonwoven web unified with a pressure-sensitive adhesive compositions; and
 e. a pattern of longitudinally extending line embossments terminating within the periphery of the shield impressed in said body-contacting surface and said sbsorptive portion to channel fluid toward the ends of the shield, said shield being adapted for attachment to a garment such that the shield will not dislodge, shift or move during wear but is removable from the garment without fabric damage or adhesive residue.

* * * * *